United States Patent [19]
Bamji et al.

[11] Patent Number: 5,533,807
[45] Date of Patent: Jul. 9, 1996

[54] MEASUREMENT OF CROSSLINKING BY-PRODUCTS IN CROSSLINKED POLYETHYLENE

[75] Inventors: Soli S. Bamji, Gloucester; A. T. Bulinski, Orleans, both of Canada

[73] Assignee: National Research Council of Canada, Ottawa, Canada

[21] Appl. No.: 323,108

[22] Filed: Oct. 14, 1994

[51] Int. Cl.$^6$ ............................ G01N 25/00; G21H 3/02
[52] U.S. Cl. ........................ 374/45; 250/459.1; 356/311
[58] Field of Search ................ 374/45, 161; 250/459.1; 356/311

[56] References Cited

U.S. PATENT DOCUMENTS

| | | | |
|---|---|---|---|
| 3,612,686 | 10/1971 | Braman et al. | 356/311 |
| 3,769,510 | 10/1973 | Kotera et al. | 250/459.1 |
| 4,507,562 | 3/1985 | Gasiot et al. | 250/459.1 |
| 4,652,143 | 3/1987 | Wickersheim et al. | 374/161 |
| 4,870,121 | 9/1989 | Bamji et al. | 524/91 |

FOREIGN PATENT DOCUMENTS

| | | | |
|---|---|---|---|
| 0082932 | 5/1984 | Japan | 250/459.1 |
| 362250339 | 10/1987 | Japan | 250/459.1 |
| 1497464 | 7/1989 | U.S.S.R. | 356/311 |

OTHER PUBLICATIONS

D'Silva, A. P. et al., "Analytical Applications of X-Ray Excited Optical Luminescence," Analytical Chemistry, vol. 6, No. 8 (Jul. 1977).

*Primary Examiner*—Diego F. F. Gutierrez
*Attorney, Agent, or Firm*—George A. Seaby

[57] ABSTRACT

At present, concentration of the crosslinking by-products crosslinked polyethylene used as insulation in high voltage cables is determined by a cumbersome, time consuming method involving taking a sample of the polymer, extracting volatile crosslinking by-products which affect the strength of the cable, and analyzing the by-products using a mass spectrometer. A novel method of in-situ measurement of the concentration of the crosslinking by-products in power cable insulation includes the step of detecting the thermo-luminescence emitted during the initial heating required to reduce the crosslinking by-products in the polymer prior to the electrical tests. Measurement of the intensity of thermoluminescence provides a direct indication of the by-product concentration which can be correlated to the electrical strength of the insulation.

7 Claims, 3 Drawing Sheets

MEASUREMENT OF CROSSLINKING BY-PRODUCTS IN CROSSLINKED POLYETHYLENE

BACKGROUND OF THE INVENTION

Field of the Invention

This invention relates to a method of determining the concentration of the crosslinking by-products in crosslinked polyethylene used in power cables.

Discussion of the Prior Art

Extruded polyethylene has been used as a dielectric in high voltage electrical cables for more than thirty years. Because of the nature of the polymer, the use of polyethylene in power cables was initially confined to distribution class cables. However, because of advances in cleanliness of materials, extrusion techniques, crosslinking methodologies and material handling, polyethylene has been used in cables of higher and higher voltages and electrical stress levels. Developments in this area have been most rapid in France and Japan where crosslinked polyethylene cables are presently used for power transmissions at voltages up to 400 and 500 kV, respectively. The next generation of high voltage polymer insulated cables are expected to ultimately operate at 1 MV.

In a crosslinked polyethylene power cable, a high current flows through a central conductor, and the insulation surrounding the conductor is subjected to high temperatures and a temperature gradient. The maximum temperature occurs adjacent to the central conductor, and under normal conditions will be 90° C. on a continuous basis and 130° C. under emergency overload conditions. The polyethylene is crosslinked to provide sufficient mechanical strength to withstand the high temperatures. Chemical crosslinking is the most commonly used technique to cross-link the polymer. However, chemical crosslinking creates by-products such as acetophenone, α-methylene styrene and cumyl alcohol. These by-products are polar compounds which can affect the electrical stress distribution in the polymer and influence the results of high voltage withstand tests performed on the cables prior to installation. Conventionally, cables are tested after production to check the integrity of the product, and the ultimate user conducts acceptance tests before energizing the cable. The crosslinking by-products such as acetophenone increase the AC breakdown voltage of the polymer and are also reported to cause space charge to be trapped upon the application of DC voltage (see Electric Power Research Institute Report TR101245). As the volatile crosslinking by-products diffuse out of the polymer the dielectric strength decreases. By the time the insulation is free of such by-products, the dielectric strength is significantly lowered (see "Effect of DC Testing on XLPE Insulated Cables", B. Bernstein, IEEE Electrical Insulation Magazine, Vol. 9, No. 4, 1993).

Because the cable user needs to know the ultimate lowest strength of the cable insulation, the general practice is to decrease the concentration of the volatile crosslinking by-products from the newly manufactured cables before they are commissioned into service. This practice helps the user to obtain more reliable data by the breakdown tests and to detect any flaws in the manufactured product. The concentration of the volatile crosslinking by-products is decreased by treating the cable for several hours at a high temperature in a vacuum oven.

The current method of determining the concentration of by-products is to cut out pieces of the cable after the high temperature treatment, extract the by-products from the polymer for several hours and then analyze them with a mass spectrometer. The method is rather cumbersome and time consuming.

GENERAL DESCRIPTION OF THE INVENTION

An object of the present invention is to provide a solution to the above-identified problem by a relatively simple, non-destructive method of determining the concentration of by-products in crosslinked polyethylene.

Another object of the invention is to provide a method of the above described type which can be performed in situ, and which is more sensitive than mass spectrometry.

Accordingly, the invention relates to a method of measuring the concentration of crosslinking by-products in crosslinked polyethylene comprising heating the polyethylene to a sufficiently high temperature to cause thermoluminescence of the crosslinking by-products; and measuring the intensity of the thermoluminescence to obtain an indication of the concentration of the crosslinking by-products and hence the ultimate strength of the polyethylene.

The invention is based on experimental studies which have demonstrated that crosslinked polyethylene cable insulation emits light when subjected to high temperatures, even in the absence of voltage application. The light is due to thermoluminescence of the crosslinking by-products and its intensity depends on the concentration of the by-products present in the polymer.

BRIEF DESCRIPTION OF THE DRAWINGS

The invention is described in greater detail hereinafter with reference to the accompanying drawings, wherein.

DESCRIPTION OF THE PREFERRED EMBODIMENT

In order to determine the sensitivity of the method, crosslinked polyethylene cable insulation containing various concentrations of the crosslinking by-products was heated and the light emitted due to thermoluminescence was monitored. The weight percent (wt %) of the by-products was measured using a mass analyzer. The results of the measurements are set out in Table 1.

TABLE 1

| | | Crosslinking By-Products in Crosslinked Polyethylene | | |
|---|---|---|---|---|
| Sample | Treatment | Aceto-phenone (wt %) | Cumyl Alcohol (wt %) | α-methylene styrene (wt %) |
| A (Un- | None (Freshly | 0.455 | 1.121 | 0.014 |

TABLE 1-continued

| | | Crosslinking By-Products in Crosslinked Polyethylene | | |
|---|---|---|---|---|
| Sample | Treatment | Acetophenone (wt %) | Cumyl Alcohol (wt %) | α-methylene styrene (wt %) |
| treated) | crosslinked polyethylene) | | | |
| B | After heating in a vacuum oven at 120° C. for 24 h | 0.007 | 0.006 | 0.003 |
| C | As in Type B and further heated in vac. oven, 90° C. for 170 h | <0.001 | 0.002 | <0.001 |

As set out in Table 1, sample B, which was heated in a vacuum oven at 120° C. for 24 hours, has a lower concentration of crosslinking by-products than the untreated polymer (sample A). Sample C was heated at 90° for an additional week and the concentration of by-products reduced below the sensitivity limit of the mass spectrometer. It is believed that acceptable results can be achieved by initially heating the insulation in a vacuum at a temperature above 50° C. for more than 24 hours. The additional heating (as in the case of Sample C) is carried out at a temperature lower than the initial heating temperature for at least an additional 48 hours.

Figure 1:
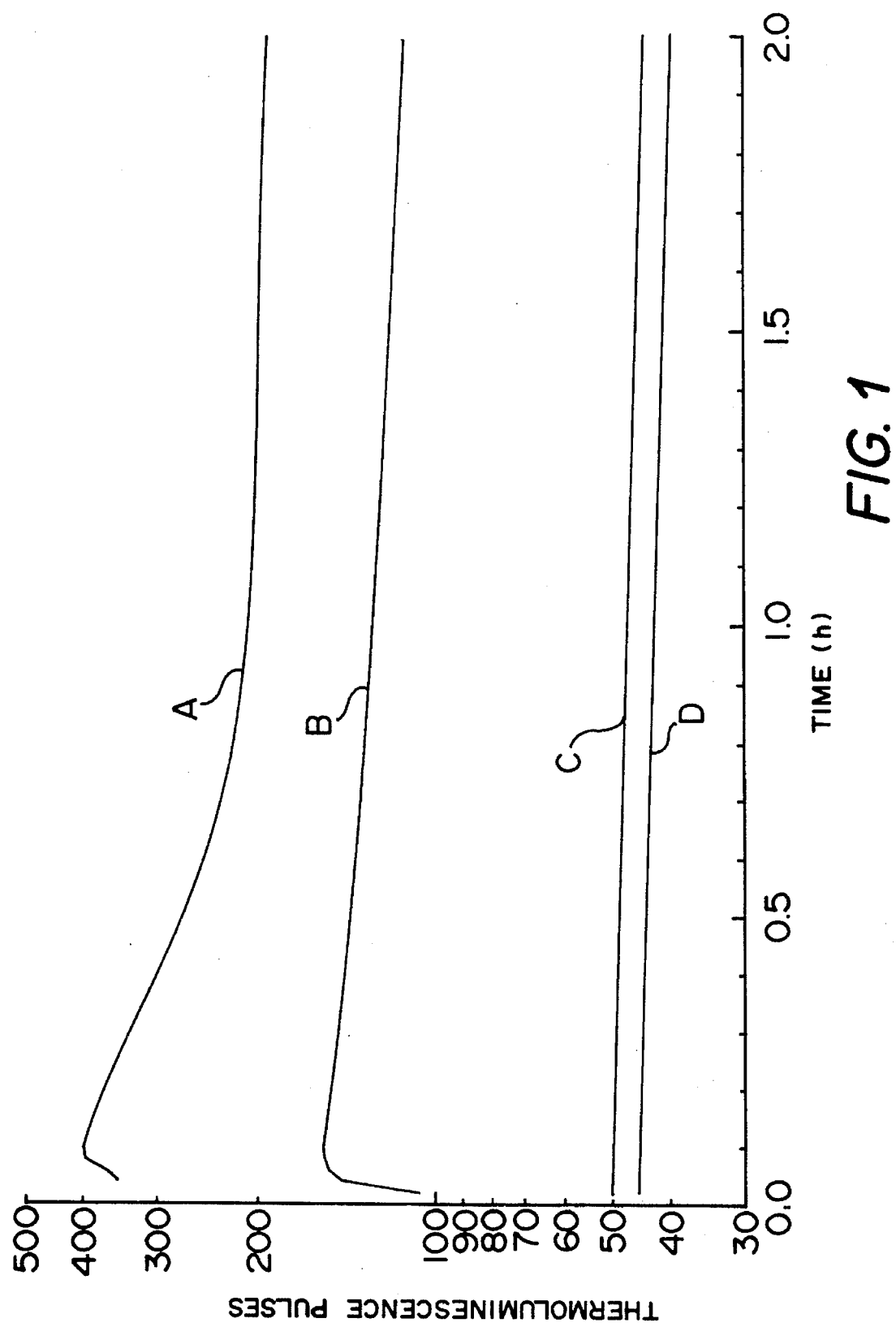
FIG. 1 is a graph of thermoluminescence versus time for a variety of crosslinked polyethylene samples.
Figure 2:
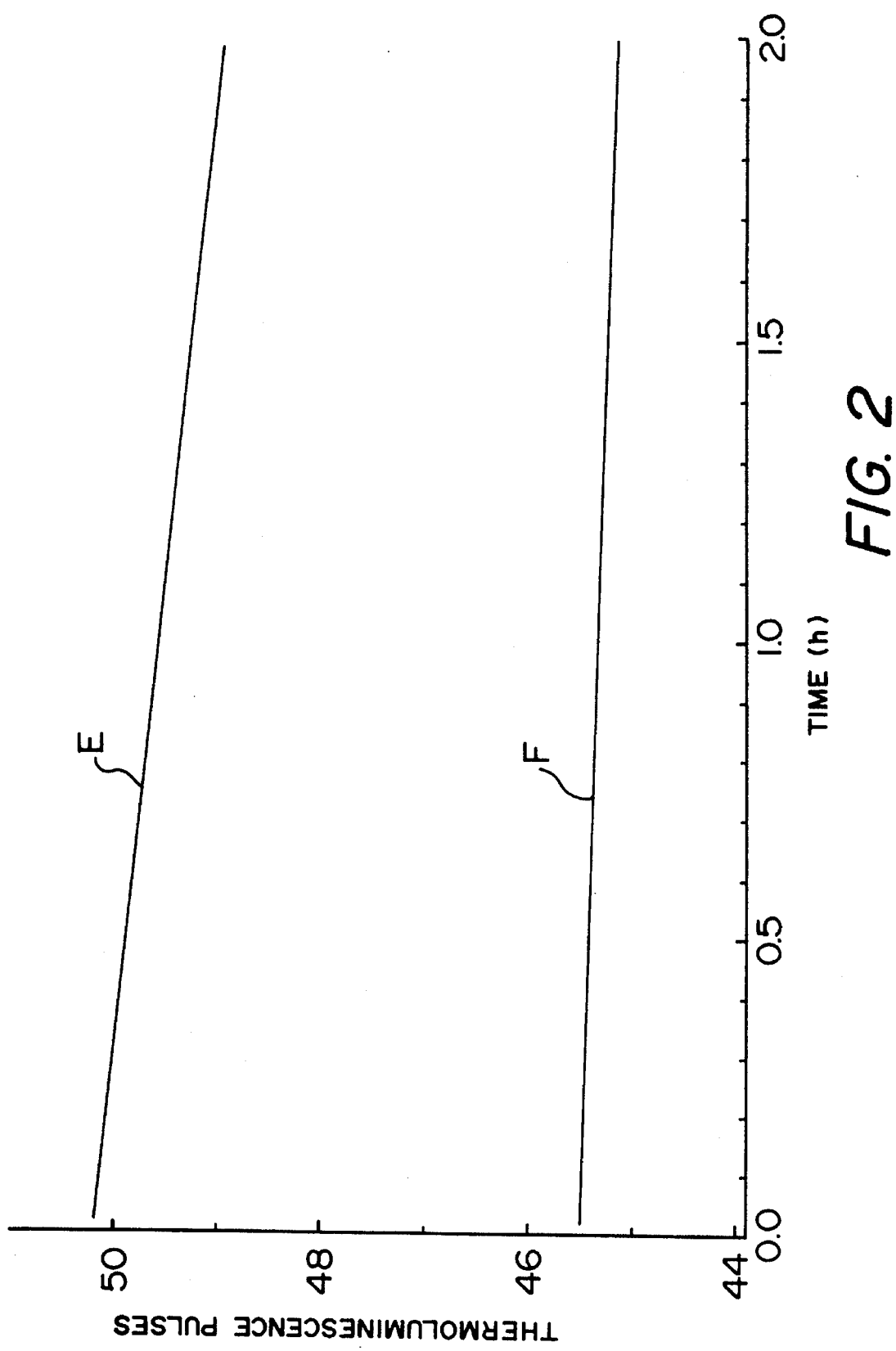
FIG. 2 is a graph of thermoluminescence on a linear scale versus time for a specific concentration of the by-products in the polymer.

The temporal behaviour of thermoluminescence from untreated crosslinked polyethylene held above ambient temperature is shown by curve A in FIG. 1. At high temperatures, as the volatile by-products exude out of the polymer the thermoluminescence decreases. Curve B shows the light emitted from sample B type crosslinked polyethylene which has a lower concentration of by-products. As expected, the number of thermoluminescence pulses is also lower than that of the untreated polymer (curve A). Curve C shows the light emitted from sample C type polymer which has a by-product concentration lower than sample B type polyethylene, while curve D represents the background noise of the light detection system. Table 1 illustrates that even though the mass spectrometer could not resolve the low concentration of crosslinking by-products in sample C crosslinked polyethylene, the thermoluminescence technique detected their presence. This is shown clearly in the graph of FIG. 2 where the intensity of thermoluminescence is plotted on a linear scale for sample C type polymer (line E) and the background noise (line F).

Figure 3:
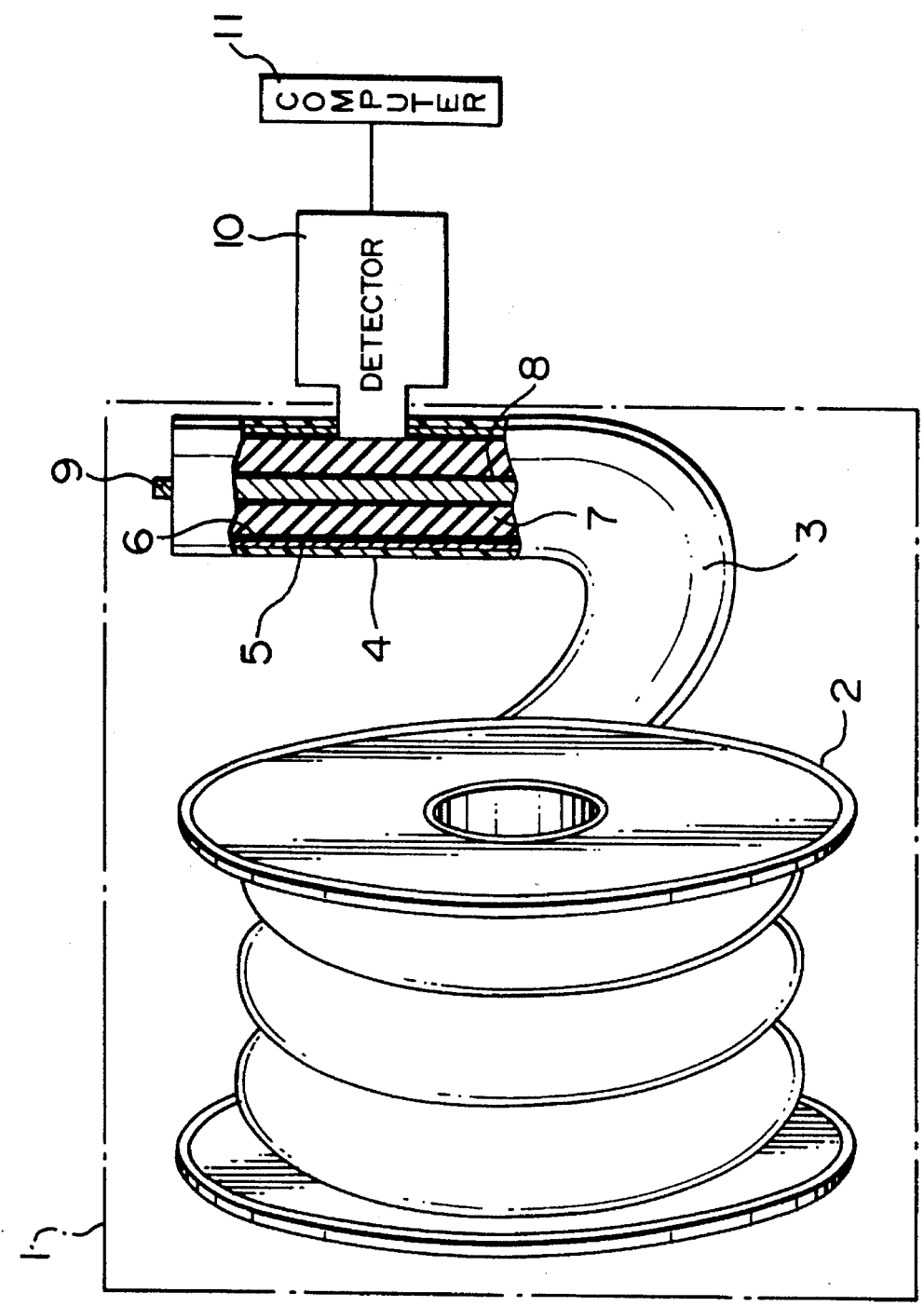
FIG. 3 is a schematic cross-sectional view of an apparatus for performing the method of the present invention.

With reference to FIG. 3, an apparatus for the in situ performance of the thermoluminescence method includes a vacuum oven 1 for receiving a spool 2 of crosslinked polyethylene insulated cable 3. The cable 3 includes an outer jacket 4 surrounding (from the outside in) a neutral conductor 5, an outer semicon shield 6, insulation 7, an inner semicon shield 8 and a central conductor 9. The insulation 7 is crosslinked polyethylene, and the semicon shields 6 and 8 are carbon loaded polymer. A window in one side of the oven 1 connects the interior of the oven to a detector 10 and a computer 11. A small area of the insulation near one end of the coiled cable 3 is exposed to the detector 10 by removing the outer jacket 4, the neutral conductor 5 and the outer semicon shield 6. The light of thermoluminescence is detected using the detector 10 in the form of a photomultiplier tube or a photodiode (not shown), which is connected to the computer 11 for continuous monitoring.

One method of monitoring the light pulses is to use an A/D interface card such as a multichannel analyzer which is inserted into the computer 11. Such a card digitizes each light pulse, determining its amplitude and time of emission. The system can be left unattended and produces a graphical display of the number of light pulses versus time. Initially, the intensity of light emitted is high, and as the crosslinking by-products exude out of the polymer, the intensity decreases. At any given time, the intensity of the thermoluminescence indicates the concentration of crosslinked by-products present in the polymer. It is suggested that the cables should be treated in vacuum for more than 24 hours at 120° C. to decrease the concentration of by-products to a level which will not affect the results of the initial high voltage tests performed on the cables prior to installation.

The advantage of the above described method is that it provides an in-situ measurement of the concentration of crosslinking by-products in power cable insulation. It is no longer necessary to cut pieces from the cable or to spend time extracting the by-products for analysis in a mass spectrometer. The intensity of the emitted light provides a direct indication of the concentration of by-products present in the cable, and the heat treatment can be stopped when the desired level has been reached. Thus, the invention also provides a method in which the intensity of the thermoluminescence is measured periodically until a predetermined low level of crosslinking by-products is reached. It is also possible to monitor the concentration of by-products at different locations in the cable, for example at the two ends thereof. This could be achieved by employing two detection systems and an interface card which can acquire data from the two systems simultaneously.

It will be appreciated that it is not always necessary to carry out a separate heating step, because the polyethylene is heated by electrical transmission in a cable.

We claim:

1. A method of measuring the concentration of crosslinking by-products in crosslinked polyethylene comprising heating the polyethylene to a sufficiently high temperature to cause thermoluminescence of the crosslinking by-products; and measuring the intensity of the thermoluminescence to obtain an indication of the concentration of the crosslinking by-products and hence the ultimate strength of the polyethylene.

2. A method according to claim 1, wherein the polyethylene is heated in a vacuum at a temperature above 50° C. for more than 24 hours.

3. A method according to claim 2, wherein the polyethylene is heated at a lower temperature for an additional 48 hours.

4. A method according to claim 1, wherein the polyethylene is heated in a vacuum at 120° C. for 24 hours.

5. A method according to claim 4, wherein the polyethylene is heated at 90° C. for an additional week.

6. A method according to claim 1, wherein the thermoluminescence is constantly monitored to provide a continuous indication of by-product concentration and consequently of the ultimate strength of the polyethylene.

7. A method according to claim 1, wherein intensity measurements are taken periodically until a predetermined low level of crosslinking by-products is reached.

* * * * *